(12) United States Patent
Fujiwara

(10) Patent No.: US 10,137,313 B2
(45) Date of Patent: Nov. 27, 2018

(54) DISPLAY APPARATUS, PORTABLE DISPLAY TERMINAL APPARATUS, AND METHOD

(71) Applicant: Panasonic Intellectual Property Management Co., Ltd., Osaka (JP)

(72) Inventor: Yuri Fujiwara, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 100 days.

(21) Appl. No.: 15/453,316

(22) Filed: Mar. 8, 2017

(65) Prior Publication Data

US 2017/0259080 A1 Sep. 14, 2017

(30) Foreign Application Priority Data

Mar. 9, 2016 (JP) ................................. 2016-046311

(51) Int. Cl.
*A61N 5/06* (2006.01)
*H04N 9/64* (2006.01)
*H04N 5/235* (2006.01)

(52) U.S. Cl.
CPC ......... *A61N 5/0618* (2013.01); *H04N 5/2354* (2013.01); *H04N 9/643* (2013.01); *H04N 9/646* (2013.01); *A61N 2005/0626* (2013.01); *A61N 2005/0663* (2013.01)

(58) Field of Classification Search
CPC combination set(s) only.
See application file for complete search history.

(56) References Cited

U.S. PATENT DOCUMENTS

2015/0051672 A1* 2/2015 Jo ............................ A61N 5/06
607/90

FOREIGN PATENT DOCUMENTS

| JP | 2003-296720 A | 10/2003 |
| JP | 2007-179517 A | 7/2007 |
| JP | 2011-118655 A | 6/2011 |
| JP | 2014-054290 A | 3/2014 |
| JP | 2014-157428 A | 8/2014 |

* cited by examiner

*Primary Examiner* — Scott T Luan
(74) *Attorney, Agent, or Firm* — McDermott Will & Emery LLP

(57) ABSTRACT

A mirror function display apparatus includes an imager that captures an image of a user, a display that displays the captured image of the user captured by the imager, a light source that emits light including treatment light toward a front side of the display, the treatment light producing a treatment effect, and a controller that controls the display, the light source, and the imager. The controller controls the light source and the imager to capture a first captured image of the user when the treatment light is emitted, and a second captured image of the user when the treatment light is not emitted. The controller corrects, in terms of a hue, the first captured image based on the second captured image so as to cause the display to display a corrected first captured image obtained by correcting the first captured image.

20 Claims, 7 Drawing Sheets

FIG. 6
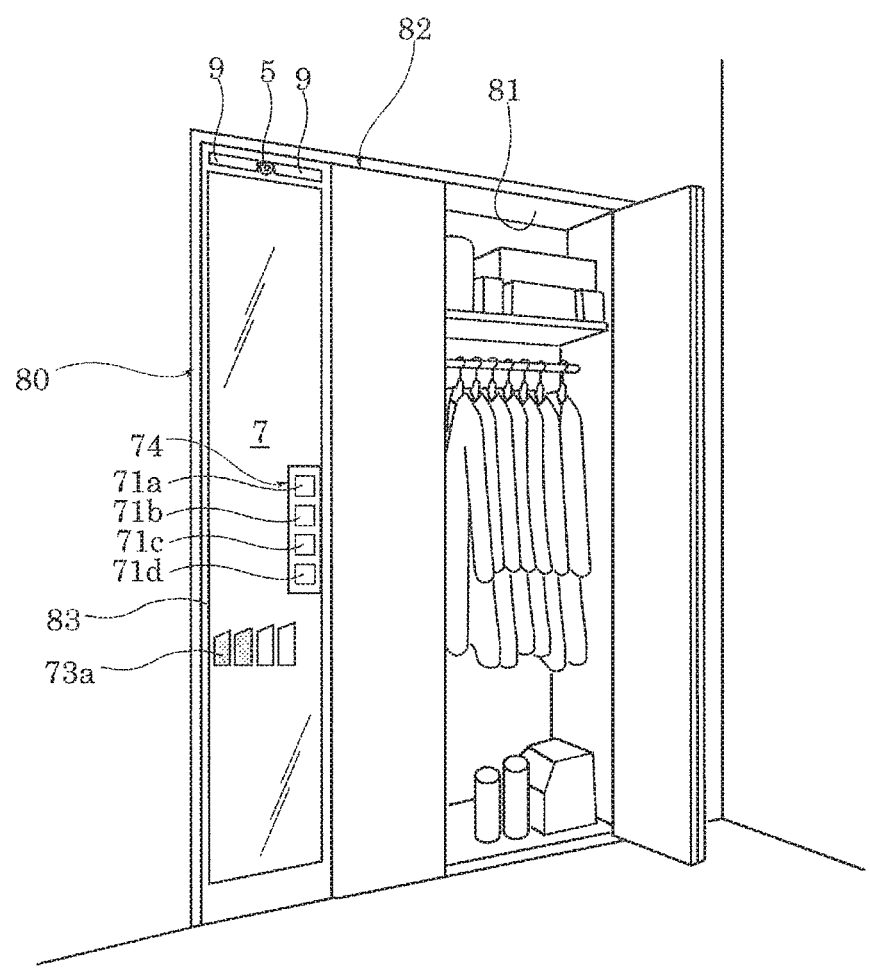
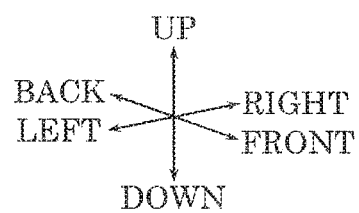

DISPLAY APPARATUS, PORTABLE DISPLAY TERMINAL APPARATUS, AND METHOD

CROSS REFERENCE TO RELATED APPLICATION

This application claims the benefit of priority of Japanese Patent Application Number 2016-046311 filed on Mar. 9, 2016, the entire content of which is hereby incorporated by reference.

BACKGROUND

1. Technical Field

The present disclosure relates to a display apparatus, a portable display terminal apparatus, and a method that reflect a user, and in particular to a display apparatus, a portable display terminal apparatus, and a method that illuminate a user, capture an image of the user and display the image.

2. Description of the Related Art

Conventionally, an image display apparatus (a display apparatus) has been known that includes a photographing part (an imager) acquiring an image (a video) of a living body, and a display part displaying the image acquired by the photographing part (see Japanese Unexamined Patent Application Publication No. 2014-157428, for example).

SUMMARY

In such a display apparatus, the user wishes to be treated while utilizing extended time for getting ready such as putting on makeup.

Accordingly, it is an object of the present disclosure to provide a display apparatus, a portable display terminal apparatus, and a method that allow a user to be treated while getting ready.

A display apparatus according to one aspect of the present disclosure includes an imager that captures an image of a user, a display that displays the captured image of the user captured by the imager, a light source that emits light including treatment light toward a front side of the display, the treatment light producing a treatment effect, and a controller that controls the display, the light source, and the imager. The controller controls the light source and the imager to capture a first captured image of the user when the treatment light is emitted, and a second captured image of the user when the treatment light is not emitted. The controller corrects, in terms of a hue, the first captured image based on the second captured image so as to cause the display to display a corrected first captured image obtained by correcting the first captured image.

Furthermore, in a portable display terminal apparatus according to one aspect of the present disclosure, the portable display terminal apparatus is the above-described display apparatus carried by the user.

The present disclosure makes it possible to provide a display apparatus and a portable display terminal apparatus that allow a user to be treated while getting ready.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 6 is a perspective view illustrating a mirror function display apparatus according to a variation of Embodiment 1;

DETAILED DESCRIPTION OF THE EMBODIMENTS

Underlying Knowledge Forming Basis of the Present Disclosure

In recent years, as a social system becomes more complicated, psychological and mental stress such as anxiety and complaint increases. Accordingly, it has become necessary to take early measures to relieve or alleviate such stress without letting it build up. Such stress is said to be caused by disturbance of a biorhythm. The biorhythm is a rhythm in which a person naturally gets sleepy at a certain time of day and naturally wakes up after certain hours of sleep, occurring as a human physiological phenomenon in a cycle of about one day.

As an effective method for improving this biorhythm, being exposed to blue-containing light (treatment light, which will be described later) for a predetermined time period or longer has been known other than getting a sleep and taking a rest. In an apparatus only emitting the treatment light, the user is merely exposed to the treatment light and does not feel enjoyment easily, so that the user gradually stops using this apparatus. Thus, such an apparatus is unlikely to cause the user to consciously and actively improve the biorhythm. As such, there is a demand for making good use of time and feeling enjoyment while being exposed to the treatment light.

On the other hand, with increasing cosmetic awareness in recent years, there are growing needs for cosmetic equipment. For example, when a user puts on makeup using the cosmetic equipment such as a cosmetic stand, the makeup may sometimes take longer time as the user enjoys changes in appearance during the makeup.

Accordingly, the present disclosure provides a display apparatus and a portable display terminal apparatus that allow the user to be treated while getting ready. In particular, women can be treated by utilizing an almost routine activity since they put on their makeup frequently.

The following is a description of embodiments of the present disclosure, with reference to the accompanying drawings. It should be noted that each embodiment described below illustrates one specific example of the present disclosure. Thus, the numerical values, shapes, materials, structural components, the arrangement and connection of the structural components mentioned in the following embodiments are merely an example and not intended to limit the present disclosure. Accordingly, among the structural components in the following embodiments, the one that is not recited in any independent claim exhibiting the most generic concept of the present disclosure will be described as an arbitrary structural component.

Incidentally, each of the figures is a schematic view and not necessarily illustrated in a strict manner. Furthermore, in each of the figures, substantially the same structures are assigned the same reference signs, and the redundant description of such structures will be omitted or simplified.

Embodiment 1

Figure 1:
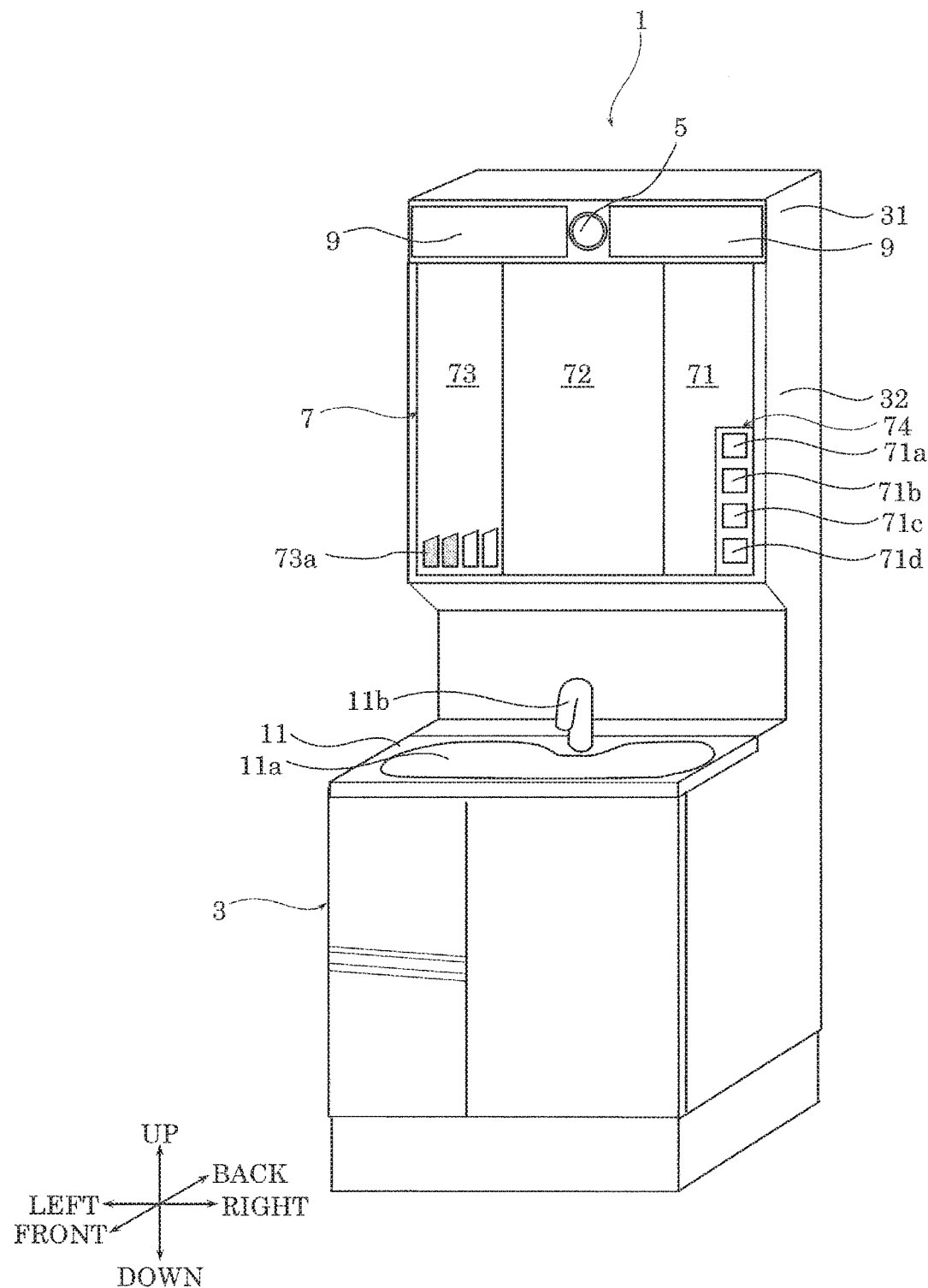
FIG. 1 is a perspective view illustrating a mirror function display apparatus according to Embodiment 1.
Figure 2:
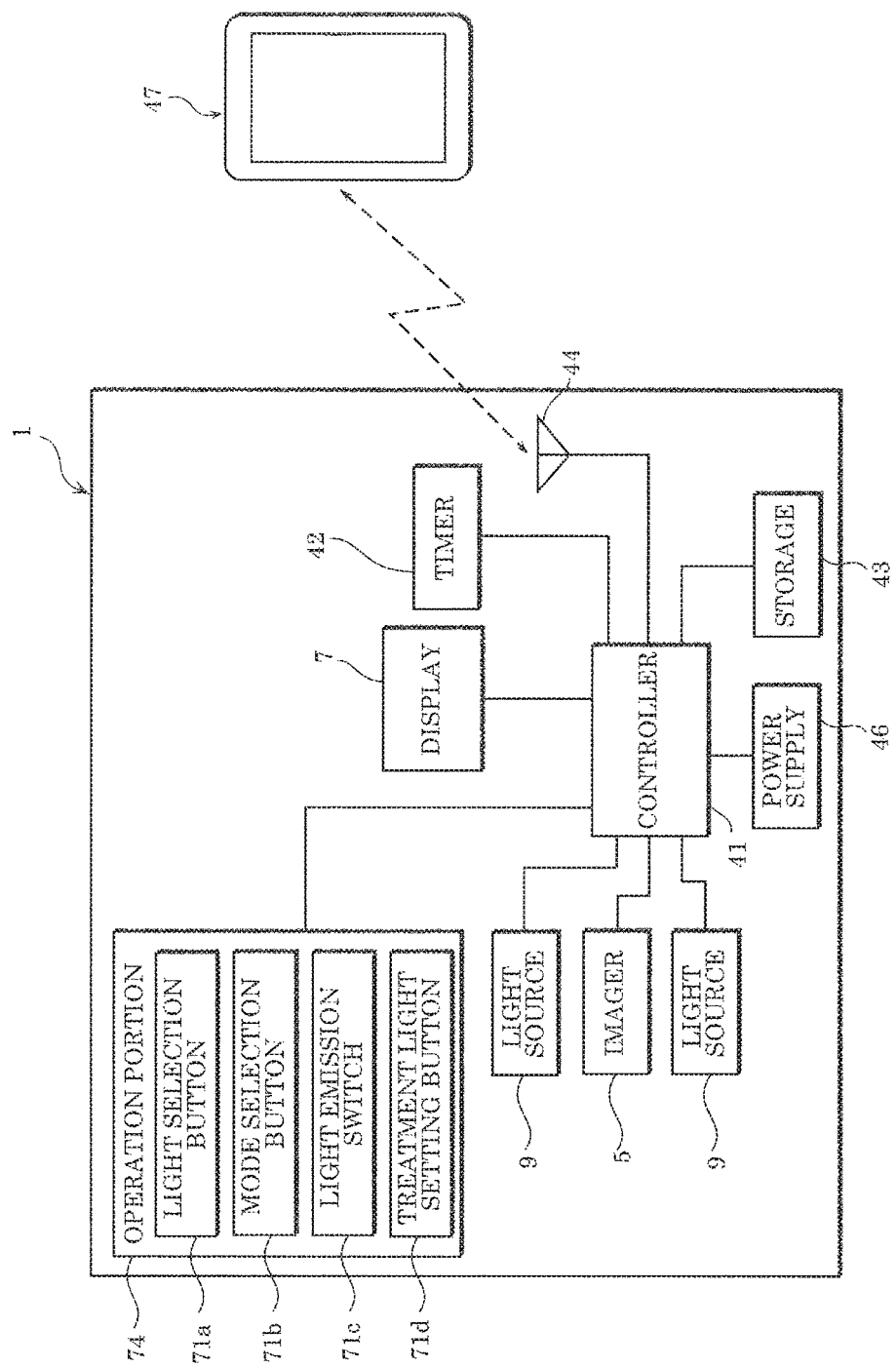
FIG. 2 is a block diagram illustrating the mirror function display apparatus according to Embodiment 1.

The following is a description of a configuration of mirror function display apparatus 1 (an example of a display apparatus) according to Embodiment 1, with reference to FIG. 1 and FIG. 2.

[Configuration]

FIG. 1 is a perspective view illustrating mirror function display apparatus 1 according to Embodiment 1. FIG. 2 is a block diagram illustrating mirror function display apparatus 1 according to Embodiment 1.

In FIG. 1, when a user views a front side of mirror function display apparatus 1, a direction heading for a left side is defined as leftward, whereby frontward, backward, horizontal, and vertical directions are indicated. Individual directions indicated in each of the figures after FIG. 1 all correspond to those indicated in FIG. 1. Incidentally, in FIG. 1, the vertical, horizontal, frontward, and backward directions vary according to a mode of use by a user, so that there is no particular limitation to these. The same applies to the figures after FIG. 1.

As illustrated in FIG. 1, mirror function display apparatus 1 (an example of the display apparatus) is an apparatus that is disposed inside a house or the like and reflects a user for allowing the user to get ready, for example, put on makeup, get dressed, wash his/her face, in front of mirror function display apparatus 1. Additionally, mirror function display apparatus 1 illuminates the user and display a captured video.

Mirror function display apparatus 1 includes main body 3, imager 5, display 7, and two light sources 9.

Main body 3 includes wash stand 11 that has a box shape and is located at a height of a waist of the user, first holder 31 having a box shape, and second holder 32 that has a plate shape and extends along the vertical direction between first holder 31 and wash stand 11.

Wash stand 11 has an inner storage space containing piping and articles, and a door, a drawer or the like for opening and closing the storage space. Wash stand 11 includes wash bowl 11a and faucet 11b.

Wash bowl 11a is fixed to an upper side of wash stand 11. Wash bowl 11a is formed of a synthetic resin or the like as one piece with wash stand 11. On a back side of wash bowl 11a, faucet 11b is provided for pouring water into wash bowl 11a. Using the water discharged from faucet 11b, activities such as washing a face, hands or clothes are performed in wash bowl 11a.

First holder 31 holds imager 5, light sources 9, and display 7.

Imager 5 is a camera for obtaining a captured image. More specifically, imager 5 includes an optical lens and an image sensor. Imager 5 causes the image sensor to convert light incident through the optical lens into an image signal, and outputs the image signal. Imager 5 is held in a central portion of first holder 31 in main body 3 so as to capture an image of a user who is located in front of display 7.

Light sources 9 are disposed on both sides of imager 5 and emit light forward of (toward a front side of) the display. In other words, light sources 9 are arranged in first holder 31 so as to illuminate the user whose image is to be captured by imager 5. Light sources 9 may be other solid-state light-emitting elements, for example, a semiconductor light-emitting element such as a light-emitting diode (LED) element or a semiconductor laser, or an electroluminescent (EL) element such as an organic EL element or an inorganic EL element.

Light sources 9 selectively emit treatment light producing a treatment effect and illumination light forward of display 7. In other words, light sources 9 emit the treatment light alone, the illumination light alone or both of the treatment light and the illumination light toward the user. This treatment light includes a peak wavelength in a blue region ranging from 380 nm to 500 nm. In particular, the treatment light can include light at a wavelength of near 480 nm. Furthermore, the illumination light is, for example, light at a wavelength in a visible light range from 380 nm to 780 nm.

Display 7 is disposed sideways on a front side of second holder 32 of main body 3 and held upright such that a display surface of display 7 faces the user. Display 7 is a mirror-shaped display, which serves as a mirror and reflects the user in a non-activated state and displays the user whose image is captured by imager 5 in an activated state. Display 7 has a flat plate shape that is elongated along the vertical direction. Display 7 includes right-hand display 71 that is held on the right side of second holder 32, left-hand display 73 that is held on the left side of second holder 32, and central display 72 that is located between right-hand display 71 and left-hand display 73. It should be noted that right-hand display 71 and left-hand display 73 may be formed as a three-fold mirror in such a manner as to pivot on the right and left of central display 72.

Central display 72 is disposed in a central portion of the front side of second holder 32, and is opposed to the user who faces mirror function display apparatus 1. Incidentally, right-hand display 71 and left-hand display 73 may be supported in a pivotable manner at both ends of central display 72 in a horizontal direction so as to be able to change their orientations relative to central display 72.

In a downward location of left-hand display 73, indicator 73a is displayed that indicates information such as remaining emission time of light sources 9, a charge amount or an emission mode. Incidentally, indicator 73a may be displayed in right-hand display 71 or central display 72.

On a lower right side of right-hand display 71, operation portion 74 is provided. Operation portion 74 includes light selection button 71a, mode selection button 71b, light emission switch 71c, and treatment light setting button 71d that are aligned along the vertical direction. Light selection button 71a is a button for selecting emission of the treatment light and the illumination light. Mode selection button 71b is a button for selecting a first operation mode or a second operation mode, which will be described later. Light emission switch 71c is a switch for causing light sources 9 to emit light. Treatment light setting button 71d can set an intensity of the treatment light through selection by the user. In other words, operation portion 74 makes it possible to, for example, select the first operation mode or the second operation mode, select the illumination light or the treatment light, set a display of indicator 73a to be shown on display 7, and set the intensity of the treatment light. It should be noted that operation portion 74 may be a mechanical push button or a capacitive touch panel that is disposed on a surface of left-hand display 73. Incidentally, operation portion 74 may be displayed on left-hand display 73 or central display 72.

It should be noted that a part of display 7 can also display white light or blue light to illuminate the user. In other words, the part of display 7 can also function as light source 9. In that case, light source 9 is not needed.

As illustrated in FIG. 2, mirror function display apparatus 1 includes not only imager 5, display 7, light sources 9, and operation portion 74 but also controller 41, timer 42, storage 43, communicator 44, and power supply 46.

Controller 41 includes, for example, a control circuit for controlling light sources 9, imager 5, display 7, storage 43, timer 42, communicator 44, and operation portion 74. Controller 41 may be configured by a processor, a microcomputer or the like.

Furthermore, through a selection (an operation of light selection button 71a) by the user, controller 41 causes light sources 9 to emit the treatment light and the illumination light.

Moreover, controller 41 receives a first captured image, which is a user's image captured by imager 5, when causing light sources 9 to emit the treatment light toward the user. The first captured image is a moving image of the user. Controller 41 also receives a second captured image, which is a user's image captured by imager 5, when causing light sources 9 to emit the illumination light toward the user. The second captured image is a still image of the user. Furthermore, controller 41 stores the generated second captured image in storage 43. Additionally, controller 41 generates a corrected first captured image, which is a video generated by correcting a hue based on the first captured image and the second captured image. The corrected first captured image is a moving image.

More specifically, controller 41 detects a portion of a user's skin from the second captured image, for example. Controller 41 calculates a map image of the hue indicating blue from the portion of the user's skin. The map image is a map arranged at a corresponding position in each pixel. Controller 41 uses as a reference this map image obtained from the second captured image. Controller 41 also calculates a map image of the hue indicating blue from a skin image in the first captured image. Controller 41 subtracts the map image of the second captured image from the map image of the first captured image, thereby calculating a correction value for correcting the hue of blue. Then, controller 41 causes storage 43 to store this correction value. Thereafter, controller 41 subtracts the correction value for correcting the hue of blue from the first captured image, thereby generating the second captured image.

Furthermore, controller 41 performs a reversal processing of right-left reversing the first captured image and the second captured image that have been captured. Controller 41 causes display 7 to display the captured image generated by right-left reversing the images obtained by imager 5. The user uses mirror function display apparatus 1 as an electronic mirror, for example, views the image displayed on display 7 as if the user were viewing a mirror.

Moreover, controller 41 causes display 7 to display the second captured image while the treatment light is emitted. Incidentally controller 41 may cause display 7 to display a captured image of the user also while the illumination light is emitted.

Additionally, controller 41 has the first operation mode and the second operation mode. Through a selection (an operation of mode selection button 71b) by the user, controller 41 switches between the first operation mode and the second operation mode.

The first operation mode is for correcting the captured image so that this image achieves brightness corresponding to a bright place such as a daytime outdoor place or an illuminated office. The first operation mode is a mode of generating a first brightness corrected image by performing a correction of increasing a brightness value of the corrected first captured image. Furthermore, when the treatment light is not emitted (the illumination light is emitted) in the first operation mode, controller 41 generates a third brightness corrected image by performing a correction of increasing a brightness value of the second captured image. The first brightness corrected image and the third brightness corrected image are moving images.

The second operation mode is for correcting the captured image so that this image achieves brightness corresponding to a dim place such as a party setting or a place at dusk. The second operation mode is a mode of generating a second brightness corrected image by performing a correction of decreasing a brightness value of the corrected first captured image. Furthermore, when the treatment light is not emitted (the illumination light is emitted) in the second operation mode, controller 41 generates a fourth brightness corrected image by performing a correction of decreasing a brightness value of the second captured image. The second brightness corrected image and the fourth brightness corrected image are moving images.

Furthermore, controller 41 calculates treatment time from the intensity of the treatment light operated by treatment light setting button 71d. Controller 41 transmits information of the calculated treatment time to timer 42. Timer 42 measures time based on the treatment time. When a predetermined period of time has elapsed since the start of measuring the time by timer 42, controller 41 transmits a treatment stop signal for stopping the emission of the treatment light to light sources 9, and transmits an illumination start signal for causing the emission of the illumination light to light sources 9. It should be noted that the treatment time shortens as the treatment light is intensified, and vice versa.

Timer 42 is connected to controller 41, and measures time during which light sources 9 emit the treatment light. Timer 42 transmits the measured time to controller 41. When the predetermined period of the measured time has elapsed, timer 42 receives a measurement stop signal from controller 41, and stops measuring the time. It should be noted that the user may be able to input the treatment time using operation portion 74.

Storage 43 is a non-volatile storage device that stores the second captured image, etc. As storage 43, a semiconductor memory, for example, a flash memory or electrically erasable programmable read-only memory (EEPROM) is used.

Communicator 44 is connected to controller 41, and wirelessly communicates with external terminal 47. External terminal 47 is, for example, a smartphone or a personal computer. Communicator 44 receives user's own physical information such as a menstrual cycle and hours of sleep that the user inputs into terminal 47 in which a dedicated application is installed. Controller 41 calculates the treatment time and the intensity of the treatment light based on the above personal information.

Although power supply 46 is appropriately supplied from a utility power system, power supply 46 may be a primary cell or a secondary cell such as a battery. Power supply 46 is connected to controller 41, and supplies power via controller 41 to each of display 7, light sources 9, storage 43 and so on.

[Operation]

The following is a description of an operation of mirror function display apparatus 1 (a method) in Embodiment 1.

Figure 3:
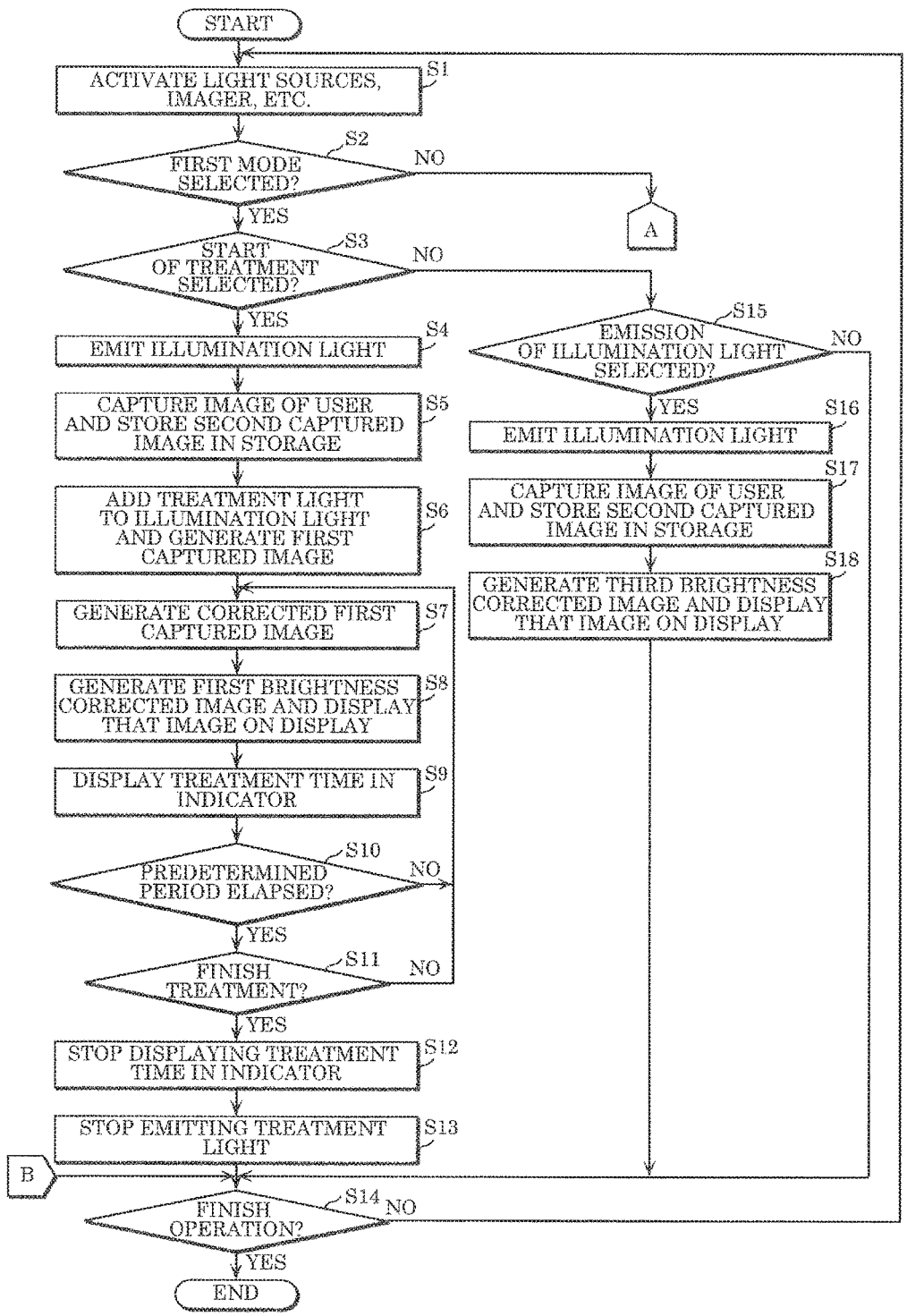
FIG. 3 is a flowchart illustrating an operation of the mirror function display apparatus according to Embodiment 1.
Figure 4:
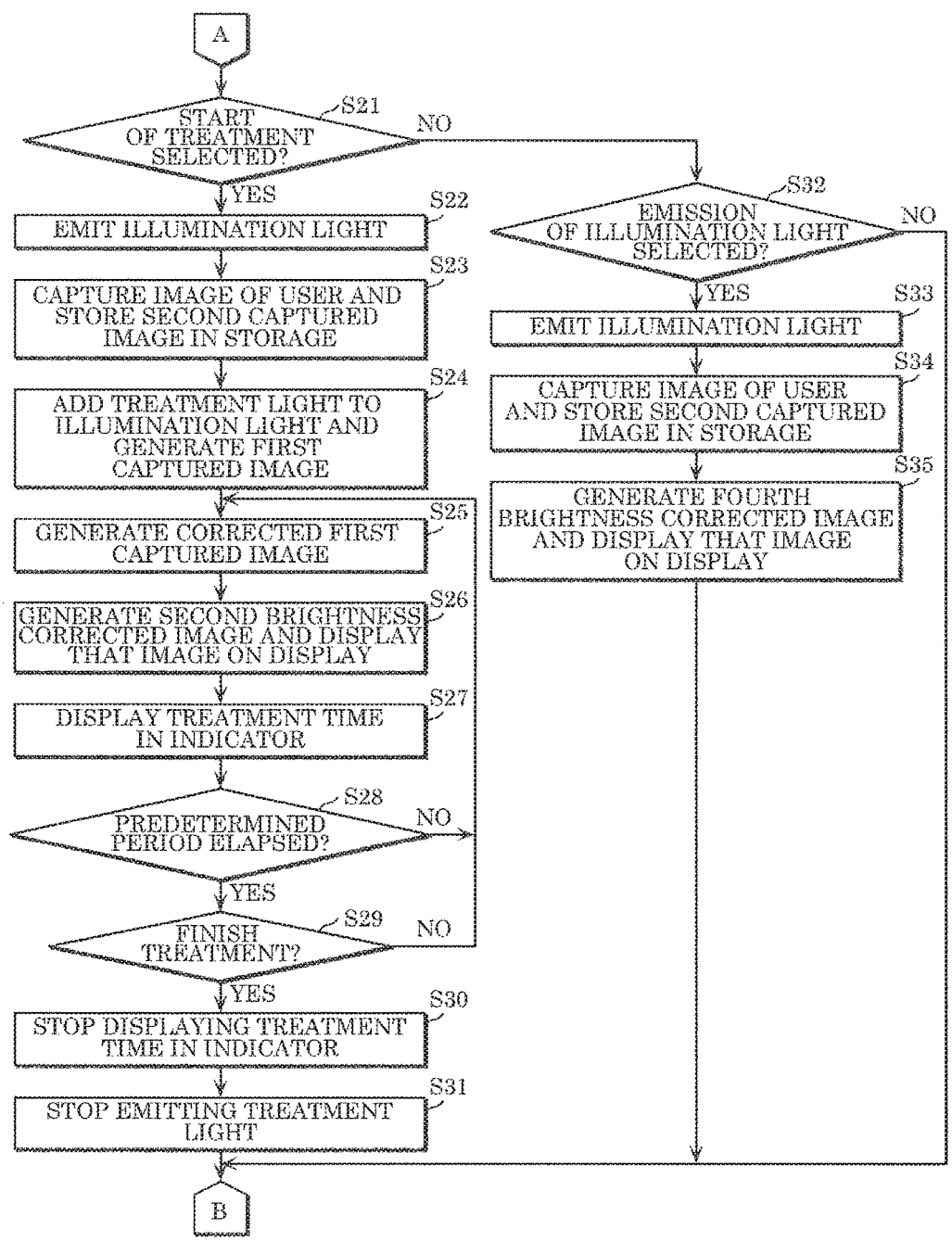
FIG. 4 is a flowchart illustrating an operation of the mirror function display apparatus according to Embodiment 1.
Figure 5:
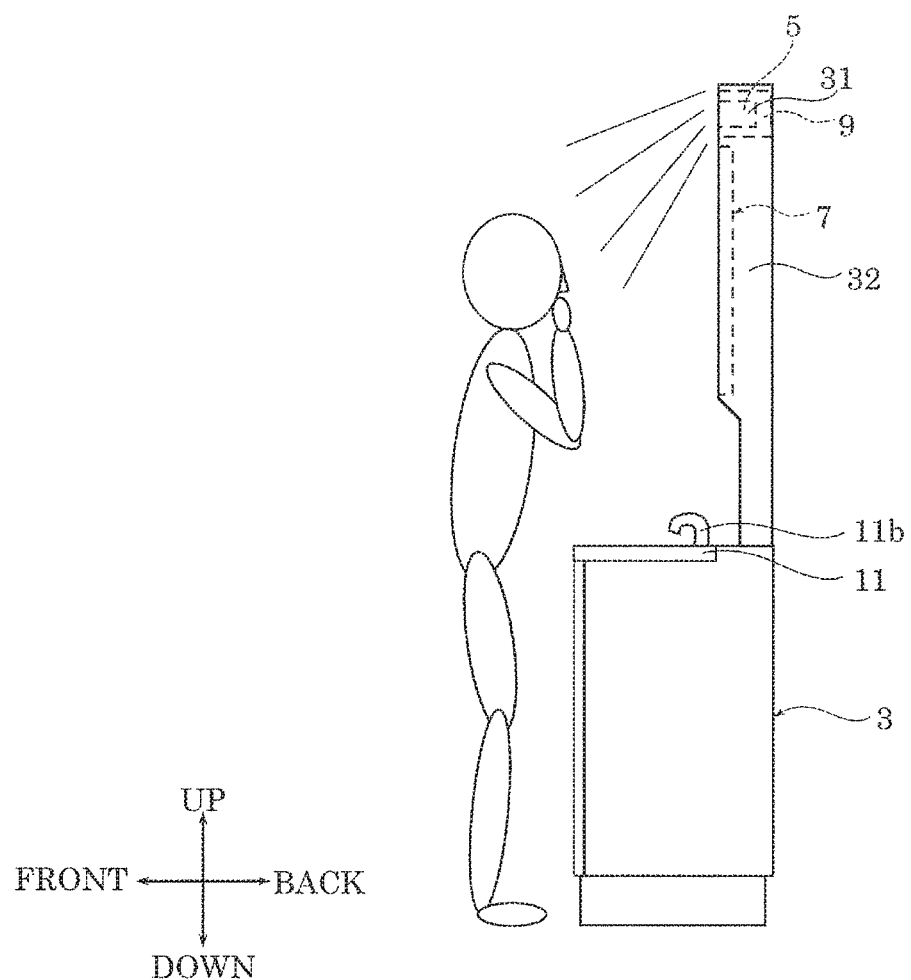
FIG. 5 illustrates an example of using the mirror function display apparatus according to Embodiment 1.

FIG. 3 is a flowchart illustrating the operation of mirror function display apparatus 1 according to Embodiment 1. FIG. 4 is a flowchart illustrating the operation of mirror function display apparatus 1 according to Embodiment 1. FIG. 5 illustrates an example of using mirror function display apparatus 1 according to Embodiment 1.

As illustrated in FIG. 3, the user first activates mirror function display apparatus 1. The user can set whether to emit the treatment light. When the user makes a setting of emitting the treatment light, a flow of mirror function display apparatus 1 is started.

Controller 41 supplies power to and activates light sources 9, imager 5, display 7, and storage 43 (S1). It should be noted that controller 41 may cause display 7 to display a screen prompting the user to select a mode. The user operates mode selection button 71b in operation portion 74 to select the first operation mode or the second operation mode. Controller 41 determines whether or not the first operation mode has been selected (S2). Here, the user selects the first operation mode or the second operation mode according to his/her purpose. The user selects the first operation mode when going to a bright place such as an office (YES in S2).

Next, controller 41 determines whether or not a start of treatment of emitting the treatment light has been selected (S3). Here, the user selects the start of treatment when the user wishes to be exposed to the treatment light while putting on makeup or the like (YES in S3). It should be noted that, before Step S3, controller 41 may cause display 7 to display a screen prompting the user to select the light to be emitted to the user.

When the start of treatment is selected in operation portion 74 (YES in S3), controller 41 causes light sources 9 to emit the illumination light (S4). Then, controller 41 causes imager 5 to capture an image of the user (S5). Imager 5 generates the second captured image serving as reference information for generating the corrected first captured image, and transmits the second captured image to controller 41. Controller 41 receives the second captured image and stores the second captured image in storage 43 (S5). Incidentally, although controller 41 causes light sources 9 to emit the illumination light in Step S4, controller 41 may also cause light sources 9 to emit the illumination light if light emission switch 71c is ON at the time of activation of mirror function display apparatus 1. In the case where there are more than one second captured image in Step S5, it may also be possible to select a favorable second captured image at the user's will before capturing the image of the user. In this case, it may be possible to skip Step S6 and proceed to a subsequent step.

After imager 5 captures the image of the user, controller 41 adds the treatment light to the illumination light emitted by light sources 9 (S6).

Controller 41 causes imager 5 to capture the image of the user toward which the treatment light is emitted. At this time, the user is shown in a bluish state. Imager 5 generates the first captured image from the captured video (S6), and transmits the first captured image to controller 41. Controller 41 receives the first captured image, and calculates the correction value from the first captured image and the second captured image. Controller 41 subtracts the correction value from the first captured image, thus generating the corrected first captured image (S7).

Controller 41 generates the first brightness corrected image having increased brightness from the corrected first captured image and the brightness value (S8). Controller 41 causes display 7 to display the first brightness corrected image (S8). Thus, display 7 does not display the user in the bluish state but displays a user video that has a hue close to the hue in the first captured image and is brighter than the first captured image even when the treatment light is emitted.

Controller 41 calculates the treatment time from an amount of the treatment light operated by treatment light setting button 71d. Controller 41 transmits information of the calculated treatment time to timer 42. Timer 42 receives this information of the treatment time, and starts measuring emission time. Furthermore, controller 41 causes display 7 to display indicator 73a for the emission time and so on (S9).

Controller 41 determines whether or not a predetermined period of the emission time has elapsed (S10). When the predetermined period of the emission time has not elapsed, the operation returns to Step S7. In other words, until after the predetermined period, controller 41 performs feedback so as to calculate the correction value and the corrected first captured image from the first captured image and the second captured image.

When the predetermined period of the emission time has elapsed (YES in S10), it can be determined that the treatment time has been finished. Incidentally, controller 41 may cause display 7 to display a screen about whether to continue the emission of the treatment light. Controller 41 determines whether to continue the emission of the treatment light (S11). When the user continues putting on makeup (wishes to be exposed to the treatment light), the operation returns to Step S7. On the other hand, when the user does not continue putting on makeup (does not wish to be exposed to the treatment light any longer), controller 41 causes display 7 to stop displaying indicator 73a of the emission time and so on (S12). Controller 41 causes light sources 9 to stop emitting the treatment light (S13). In other words, light sources 9 are now emitting the illumination light. Then, the operation proceeds to subsequent Step S14. Incidentally, without making the determination in Step S11, it may also be possible to stop emitting the treatment light once the predetermined period of time has elapsed.

Furthermore, when the start of treatment has not been selected in operation portion 74 (NO in S3), controller 41 determines whether or not the selection of causing light sources 9 to emit the illumination light has been made (S15). When the selection of causing light sources 9 to emit the illumination light has been made (YES in S15), controller 41 causes light sources 9 to emit the illumination light (S16). Then, controller 41 causes imager 5 to capture an image of the user (S17). Imager 5 generates and transmits the second captured image to controller 41. Controller 41 receives the second captured image and stores the second captured image in storage 43 (S17).

Controller 41 generates the third brightness corrected image by performing the correction of increasing the brightness value of the second captured image, from the second captured image and the brightness value. Then, controller 41 causes display 7 to display the third brightness corrected image (818). Thus, display 7 displays the user subjected to the correction so as to achieve brightness corresponding to the bright place such as an office.

When the selection of causing light sources 9 to emit the illumination light has not been made (NO in S15), controller 41 proceeds to Step S14.

As illustrated in FIG. 4, when the user selects the second operation mode (NO in S2), controller 41 determines whether or not the start of treatment of emitting the treatment light has been selected (S21). Here, the user selects the start of treatment when the user wishes to be exposed to the treatment light while putting on makeup or the like (YES in S21).

When the start of treatment is selected in operation portion 74 (YES in S21), controller 41 causes light sources 9 to emit the illumination light (S22). Then, controller 41 causes imager 5 to capture an image of the user (S23). Imager 5 generates the second captured image serving as reference information for generating the corrected first captured image, and transmits the second captured image to controller 41. Controller 41 receives the second captured image and stores the second captured image in storage 43 (S23).

After imager 5 captures the image of the user, controller 41 adds the treatment light to the illumination light as light emitted by light sources 9 (S24).

Controller 41 causes imager 5 to capture the image of the user toward which the treatment light is emitted. Imager 5 generates the first captured image from the captured video (S24), and transmits the first captured image to controller 41. Controller 41 receives the first captured image, and calculates the correction value from the first captured image and the second captured image. Controller 41 subtracts the correction value from the first captured image, thus generating the corrected first captured image (S25).

Controller 41 generates the second brightness corrected image having decreased brightness from the corrected first captured image and the brightness value (S26). Controller 41 causes display 7 to display the second brightness corrected image (S26). Thus, display 7 does not display the user in the bluish state but displays a user video that has a hue close to the hue captured in the first captured image and is dimmer than the first captured image even when the treatment light is emitted.

Controller 41 calculates the treatment time from the amount of the treatment light operated by treatment light setting button 71d. Controller 41 transmits the information of the calculated treatment time to timer 42. Timer 42 measures time based on the treatment time. Furthermore, controller 41 causes display 7 to display indicator 73a for the emission time and so on (S27).

Controller 41 determines whether or not the predetermined period of the emission time has elapsed (S28). When the predetermined period of the emission time has not elapsed, the operation returns to Step S25. In other words, until after the predetermined period, controller 41 performs feedback so as to calculate the correction value and the corrected first captured image from the first captured image and the second captured image.

When the predetermined period of the emission time has elapsed (YES in S28), it can be determined that the treatment time has been finished. Incidentally, controller 41 may cause display 7 to display a screen about whether to continue the emission of the treatment light. Controller 41 determines whether to continue the emission of the treatment light (S29). When the user continues putting on makeup (wishes to be exposed to the treatment light), the operation returns to Step S25. On the other hand, when the user does not continue putting on makeup (does not wish to be exposed to the treatment light any longer), controller 41 causes display 7 to stop displaying indicator 73a of the emission time and so on (S30). Controller 41 causes light sources 9 to stop emitting the treatment light (S31). In other words, light sources 9 are now emitting the illumination light. Then, the operation proceeds to Step S14 in FIG. 3. Incidentally, without making the determination in Step S29, it may also be possible to stop emitting the treatment light once the predetermined period of time has elapsed.

Furthermore, when the start of treatment has not been selected in operation portion 74 (NO in S21), controller 41 determines whether or not the selection of causing light sources 9 to emit the illumination light has been made (S32). When the selection of causing light sources 9 to emit the illumination light has been made (YES in S32), controller 41 causes light sources 9 to emit the illumination light (S33). Then, controller 41 causes imager 5 to capture an image of the user (S34). Imager 5 generates and transmits the second captured image to controller 41. Controller 41 receives the second captured image and stores the second captured image in storage 43 (S34).

Controller 41 generates the fourth brightness corrected image by performing the correction of decreasing the brightness value of the second captured image, from the second captured image and the brightness value (S35). Then, controller 41 causes display 7 to display the fourth brightness corrected image (S35). Thus, display 7 displays the user subjected to the correction so as to achieve brightness corresponding to the dim place such as a party setting or a place at dusk.

When the selection of causing light sources 9 to emit the illumination light has not been made (NO in S32), controller 41 proceeds to Step S14 in FIG. 3.

As illustrated in FIG. 3, controller 41 determines whether or not selection of finishing the operation has been made (S14). When the user wishes to finish the operation (YES in S14), the user makes the selection of finishing the operation, thus ending this flow. It should be noted that, before Step S14, controller 41 may cause display 7 to display a screen prompting the user to select whether the operation should be finished or continued.

On the other hand, when the user wishes to continue the operation (NO in S14), the user makes the selection of continuing the operation, thus returning to Step S1.

Advantageous Effects

The following is a description of advantageous effects of mirror function display apparatus 1 in Embodiment 1.

As described above, mirror function display apparatus 1 according to Embodiment 1 includes imager 5 that captures an image of a user, display 7 that displays the captured image of the user captured by imager 5, light source 9 that emits light including treatment light toward a front side of display 7, the treatment light producing a treatment effect, and controller 41 that controls display 7, light source 9, and imager 5. Controller 41 controls light source 9 and imager 5 to capture a first captured image of the user when the treatment light is emitted, and a second captured image of the user when the treatment light is not emitted. Controller 41 corrects, in terms of a hue, a first captured image based on a second captured image so as to cause display 7 to display a corrected first captured image obtained by correcting the first captured image.

With this configuration, the corrected first captured image is generated from the first captured image and the second captured image, and displayed on display 7. Thus, even when the treatment light is emitted toward the user, the user can be treated while getting ready such as putting on makeup or the like.

Using this mirror function display apparatus 1, the user can be treated while getting ready, thus making good use of the time, resulting in enhanced user convenience.

Furthermore, in mirror function display apparatus 1 according to Embodiment 1, controller 41 sets one of a first operation mode of generating a first brightness corrected image by performing a correction of increasing a brightness value of the corrected first captured image, and a second operation mode of generating a second brightness corrected image by performing a correction of decreasing a brightness value of the corrected first captured image.

With this configuration, since the user is displayed on display 7 according to the user's purpose, the user can get ready more easily.

Especially when the user puts on makeup, an appropriate makeup can be achieved more easily.

Moreover, mirror function display apparatus 1 according to Embodiment 1 includes storage 43 that stores the second captured image.

With this configuration, if storage 43 stores the second captured image that has been captured in advance, it is possible to generate the corrected first captured image based on this second captured image. Accordingly, even when a use environment varies, unevenness does not show up easily in the corrected first captured image.

Additionally, mirror function display apparatus 1 according to Embodiment 1 further includes timer 42 that measures time during which light source 9 emits the treatment light. Controller 41 causes light source 9 to stop emitting the treatment light when a predetermined period of time has elapsed since a start of measuring the time by timer 42.

With this configuration, once the treatment time is finished, the emission of the treatment light stops automatically, thus providing excellent usability. In particular, by displaying the treatment time using indicator 73a, it becomes possible to provide information such as remaining treatment time.

Furthermore, in mirror function display apparatus 1 according to Embodiment 1, display 7 displays an indicator that indicates time during which the treatment light is emitted.

With this configuration, indicator 73a allows the user to obtain information such as the treatment time and remaining battery life, thus providing excellent usability.

Moreover, mirror function display apparatus 1 according to Embodiment 1 includes communicator 44 that wirelessly communicates with external terminal 47.

With this configuration, mirror function display apparatus 1 can receive personal information such as menstrual cycle or hours of sleep inputted using external terminal 47.

In particular, controller 41 can treat the user based on this personal information.

The treatment light emitted by light source 9 includes a peak wavelength in a blue region.

Light source 9 further emits illumination light having different wavelength characteristic than the treatment light toward the user.

The first captured image is captured when both the treatment light and the illumination light are emitted, and the second captured image is captured when the treatment light is not emitted and the illumination light is emitted.

The treatment light causes a hue of the first captured image different from a hue of the second captured image.

The corrected first captured image is a video.

Controller 41 sets one of plural operation modes having different hue parameters from each other, and controller 41 further corrects the first corrected captured image by using a hue parameter corresponding to a set operation mode.

The second captured image is a still image.

Mirror function display apparatus 1 further includes a timer that measures time during which light source 9 emits the treatment light. Controller 41 causes light source 9 to stop emitting the treatment light when a predetermined period of time has elapsed since a start of measuring the time by the timer.

When light source 9 stops emitting the treatment light, controller 41 stops correcting the first captured image based on the second captured image, and corrects the first captured image by using the hue parameter corresponding to the set operation mode.

Display 7 displays an indicator that indicates remaining time until the treatment light stops.

Display 7 functions as a mirror when controller 41 is turned off.

A method includes illuminating the user with a first light having first wavelength characteristics, capturing a first captured image of the user when the first light is illuminated, capturing a second captured image of the user when the first light is not illuminated, correcting a hue of the first captured image based on the second captured image, and displaying a corrected first captured image on a mirror function display.

The method further includes illuminating the user with a second light having different wavelength characteristics than the first wavelength characteristics. The first captured image is captured when the first and second lights are illuminated, and the second captured image is captured when the first light is not illuminated and the second light is illuminated.

Variation of Embodiment 1

[Configuration]

The following is a description of a configuration of mirror function display apparatus 1 according to a variation of Embodiment 1, with reference to FIG. 6.

FIG. 6 is a perspective view illustrating mirror function display apparatus 1 according to the variation of Embodiment 1. FIG. 6 illustrates a state in which opening/closing portion 82 on which display 7 is disposed is closing storing portion 81.

As illustrated in FIG. 6, mirror function display apparatus 1 is incorporated in closet 80. Closet 80 includes storing portion 81 and a pair of opening/closing portions 82. Opening/closing portions 82 include two elongated plates 83, and open or close storing portion 81.

Mirror function display apparatus 1 is incorporated in plate 83. On a front surface of plate 83, display 7 is held upright. Display 7 is formed to have a shape elongated along the vertical direction so as to reflect an entire body of the user.

Imager 5 and light sources 9 are provided upward of display 7. Imager 5 is held so as to capture an image of the user who is located in front of display 7. Light sources 9 are disposed on both sides of imager 5. Light sources 9 are provided so as to emit light forward of display 7.

Since the operation of this mirror function display apparatus 1 is similar to that of mirror function display apparatus 1 according to Embodiment 1, the description thereof will be omitted.

The advantageous effects of this mirror function display apparatus 1 are similar to those of mirror function display apparatus 1 according to Embodiment 1. Thus, the same advantageous effects will not be detailed herein.

Embodiment 2

[Configuration]

Figure 7:
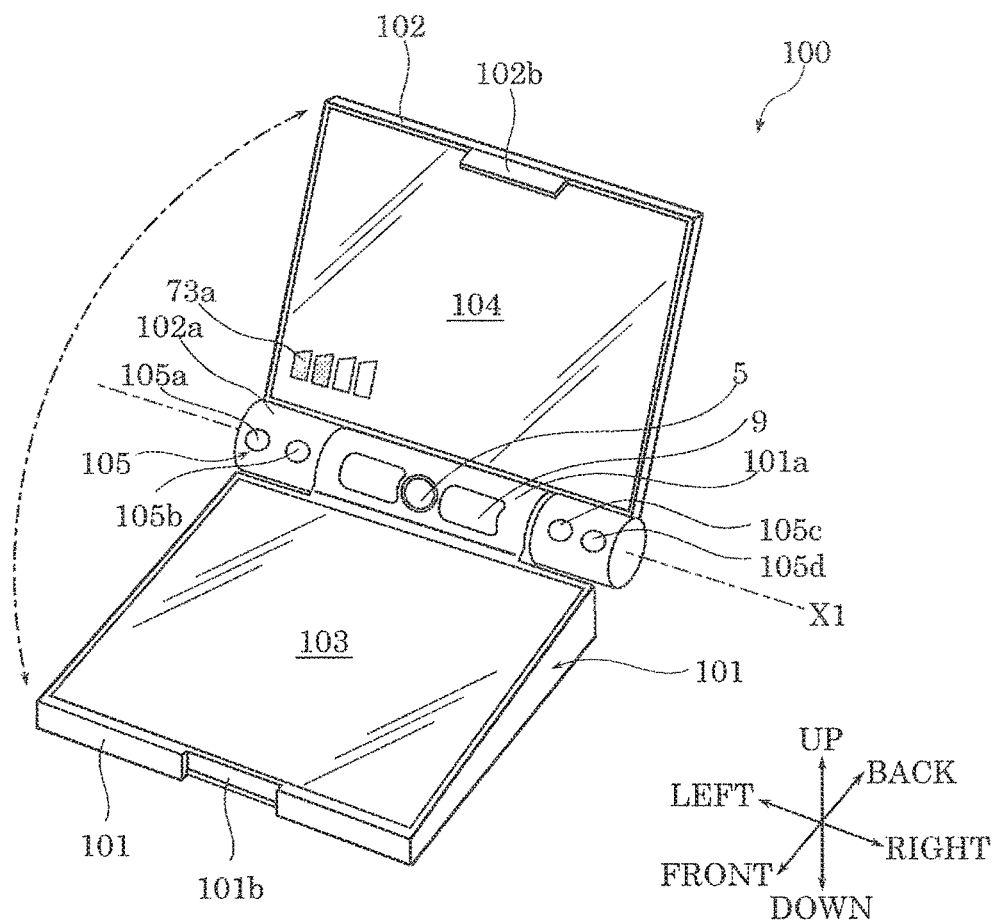
FIG. 7 is a perspective view illustrating a mirror function portable display terminal apparatus according to Embodiment 2.
Figure 8:
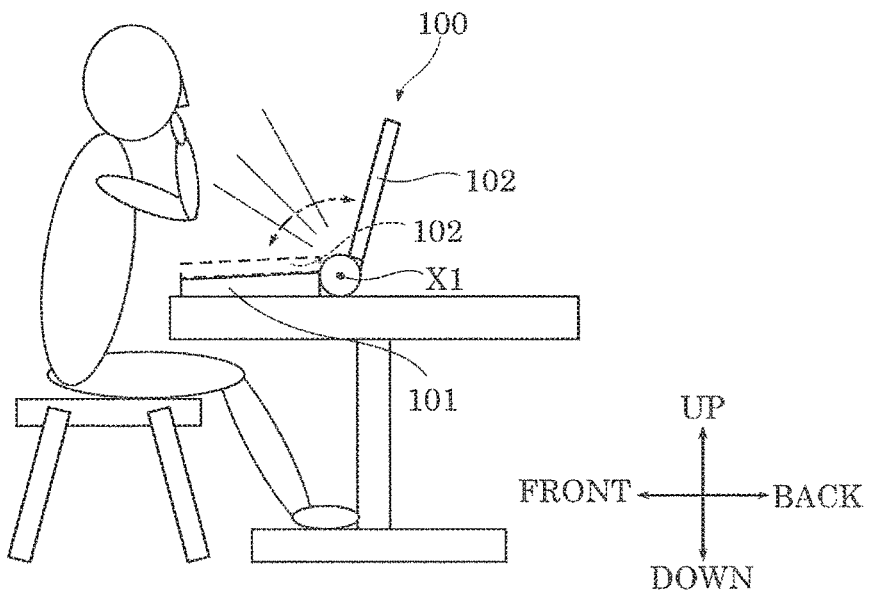
FIG. 8 illustrates an example of using the mirror function portable display terminal apparatus according to Embodiment 2.

The following is a description of a configuration of mirror function portable display terminal apparatus 100 (an example of a portable display terminal apparatus) according to Embodiment 2, with reference to FIG. 7 and FIG. 8.

FIG. 7 is a perspective view illustrating mirror function portable display terminal apparatus 100 according to Embodiment 2. FIG. 7 illustrates a state in which holder 102 is open relative to main body 101. FIG. 8 illustrates an example of using mirror function portable display terminal apparatus 100 according to Embodiment 2.

In Embodiment 2, other configurations of mirror function portable display terminal apparatus 100 are similar to those of mirror function display apparatus 1 according to Embodiment 1. Thus, the same structural components will be assigned the same reference signs, and a detailed description thereof concerning their configurations will be omitted.

As illustrated in FIG. 7, mirror function portable display terminal apparatus 100 is a tabletop apparatus that can be carried by the user. Mirror function portable display terminal apparatus 100 includes main body 101, holder 102, first display 103, second display 104, two light sources 9, and imager 5.

Main body 101 has a flat plate shape, and first display 103 is disposed on an upper surface of main body 101. Main body 101 is placed on a table in FIG. 8. Main body 101 includes main body hinge 101a that pivotably supports holder 102. Main body hinge 101a is disposed in a central portion toward a back of main body 101. Main body hinge 101a holds holder 102 at a predetermined position when holder 102 pivots relative to main body 101.

Main body hinge 101a includes imager 5 and two light sources 9. Imager 5 is held such that a central portion of main body hinge 101a can capture an image of the user who is located in front of first display 103.

Furthermore, light sources 9 are disposed on both sides of imager 5, and can emit light forward of the display.

Holder 102 can pivot about axis X1 relative to main body hinge 101a of main body 101. Holder 102 holds second display 104. Second display 104 is similar to first display 103. By a pivoting angle of holder 102, holder 102 holds second display 104 so that a display surface of second display 104 faces the user. In holder 102, a pair of holder hinges 102a are formed toward main body 101. Both of holder hinges 102a are supported pivotably relative to main body hinge 101a.

Both of holder hinges 102a include operation portion 105. Operation portion 105 includes four buttons.

Holder hinge 102a on a left side includes light selection button 105a for selecting the emissions of the treatment light and the illumination light as to the light emitted by light sources 9, and mode selection button 105b for selecting the first operation mode or the second operation mode.

Holder hinge 102a on a right side includes light emission switch 105c for causing light sources 9 to emit light, and treatment light setting button 105d for setting an intensity of the treatment light. When the user wishes to be exposed to the light, the user turns ON light emission switch 105c, and operates light selection button 105a to select the light to be emitted (the treatment light or the illumination light). When the user wishes to stop the light emission, the user turns OFF light emission switch 105c. When the user wishes to intensify the treatment light, the user raises the intensity of treatment light setting button 105d. When the user wishes to diminish the treatment light, the user lowers the intensity of treatment light setting button 105d.

In first display 103 and second display 104, the user is displayed in such a manner as to be split by main body hinge 101a and holder hinges 102a.

Furthermore, main body 101 includes latch part 101b that engages with engagement part 102b of holder 102. When engagement part 102b of holder 102 and latch part 101b engage with each other at the time of closing (folding) holder 102 with respect to main body 101, a motion in which holder 102 opens relative to main body 101 is restricted.

Main body 101 contains controller 41, timer 42, storage 43, communicator 44, operation portion 105, and power supply 46 similar to those in Embodiment 1 in FIG. 2.

Although it is appropriate that power supply 46 should be a primary cell or a secondary cell such as a battery, power supply 46 may be an external power source such as a personal computer or a utility power system.

As illustrated in FIG. 8, the user places mirror function portable display terminal apparatus 100 on the table, and causes holder 102 to pivot. The user activates mirror function portable display terminal apparatus 100, and gets ready, for example, puts on makeup.

Likewise, since the operation of this mirror function portable display terminal apparatus 100 is similar to that of mirror function display apparatus 1 according to Embodiment 1, the description thereof will be omitted.

Advantageous Effects

Now, the following is a description of advantageous effects of mirror function portable display terminal apparatus 100 in Embodiment 2.

As described above, mirror function portable display terminal apparatus 100 according to Embodiment 2 is an apparatus carried by the user.

With this configuration, the user can carry mirror function portable display terminal apparatus 100, thus providing excellent usability.

The advantageous effects of this mirror function portable display terminal apparatus 100 are similar to those of mirror function display apparatus 1 according to Embodiment 1. Thus, the same advantageous effects will not be detailed herein.

Other Variations, Etc.

The above description has been directed to the display apparatuses according to the present disclosure based on Embodiment 1, Embodiment 2, and the variation of Embodiment 1. However, the present disclosure is by no means limited to Embodiment 1, Embodiment 2, and the variation of Embodiment 1 above.

In the above-described embodiments, when the user merely wishes to be exposed to the treatment light and the illumination light, the user may turn ON light emission switch 71c without selecting the first operation mode or the second operation mode, and operate light selection button 71a so as to emit the treatment light and the illumination light.

Furthermore, in the above-described embodiments, it may also be possible to stop the emission of the illumination light in Steps S6 and S24, thereby switching to the emission of the treatment light alone.

Moreover, the display apparatus can be achieved not only as a display apparatus but also as a display method and a program that causes a personal computer to execute the display method.

Additionally, in the above-described embodiments, the controller includes the first operation mode and the second operation mode. However, the controller may further include other modes such as a third operation mode for a state brighter than the first operation mode and a fourth operation mode for a state darker than the second operation mode, for example. Moreover, the controller may also include a fifth mode or more.

Other than the above, a mode obtained by making various modifications conceivable by a person skilled in the art to Embodiment 1, Embodiment 2, and the variation of Embodiment 1 and a mode configured by any combination of the structural components and functions in Embodiment 1, Embodiment 2, and the variation of Embodiment 1 as long as not departing from the purport of the present disclosure fall within the scope of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A display apparatus comprising:
   an imager that captures an image of a user;
   a display that displays the captured image of the user captured by the imager;
   a light source that emits light including treatment light toward a front side of the display, the treatment light producing a treatment effect; and
   a controller that controls the display, the light source, and the imager, wherein:
   the controller controls the light source and the imager to capture a first captured image of the user when the treatment light is emitted, and a second captured image of the user when the treatment light is not emitted, and
   the controller corrects, in terms of a hue, the first captured image based on the second captured image so as to cause the display to display a corrected first captured image obtained by correcting the first captured image.

2. The display apparatus according to claim 1, wherein the treatment light emitted by the light source includes a peak wavelength in a blue region.

3. The display apparatus according to claim 1, wherein the light source further emit illumination light having different wavelength characteristic than the treatment light toward the user.

4. The display apparatus according to claim 3, wherein:
   the first captured image is captured when both the treatment light and the illumination light are emitted, and
   the second captured image is captured when the treatment light is not emitted and the illumination light is emitted.

5. The display apparatus according to claim 1, wherein the treatment light causes a hue of the first captured image different from a hue of the second captured image.

6. The display apparatus according to claim 1, wherein the corrected first captured image is a video.

7. The display apparatus according to claim 6, wherein:
   the controller sets one of plural operation modes having different hue parameters from each other, and
   the controller further corrects the first corrected captured image by using a hue parameter corresponding to a set operation mode.

8. The display apparatus according to claim 7,
   wherein the controller sets one of:
   a first operation mode of generating a first brightness corrected image by performing a correction of increasing a brightness value of the corrected first captured image, and
   a second operation mode of generating a second brightness corrected image by performing a correction of decreasing a brightness value of the corrected first captured image.

9. The display apparatus according to claim 7, further comprising
   a timer that measures time during which the light source emits the treatment light,
   wherein the controller causes the light source to stop emitting the treatment light when a predetermined period of time has elapsed since a start of measuring the time by the timer.

10. The display apparatus according to claim 9, wherein when the light source stops emitting the treatment light, the controller stops correcting the first captured image based on the second captured image, and corrects the first captured image by using the hue parameter corresponding to the set operation mode.

11. The display apparatus according to claim 1, further comprising
    a storage that stores the second captured image.

12. The display apparatus according to claim 1, wherein the second captured image is a still image.

13. The display apparatus according to claim 1, further comprising
    a timer that measures time during which the light source emits the treatment light,
    wherein the controller causes the light source to stop emitting the treatment light when a predetermined period of time has elapsed since a start of measuring the time by the timer.

14. The display apparatus according to claim 13,
    wherein the display displays an indicator that indicates remaining time until the treatment light stops.

15. The display apparatus according to claim 1,
    wherein the display displays an indicator that indicates time during which the treatment light is emitted.

16. The display apparatus according to claim 1, further comprising
    a communicator that wirelessly communicates with an external terminal.

17. A portable display terminal apparatus,
    which is the display apparatus according to claim 1 carried by the user.

18. The display apparatus according to claim 1, wherein the display functions as a mirror when the controller is turned off.

19. A method comprising:
    illuminating the user with a first light having first wavelength characteristics;
    capturing a first captured image of the user when the first light is illuminated;
    capturing a second captured image of the user when the first light is not illuminated;
    correcting a hue of the first captured image based on the second captured image; and
    displaying a corrected first captured image on a mirror function display.

20. The method of claim 19, further comprising illuminating the user with a second light having different wavelength characteristics than the first wavelength characteristics, wherein the first captured image is captured when the first and second lights are illuminated, and the second captured image is captured when the first light is not illuminated and the second light is illuminated.

* * * * *